(12) United States Patent
Wu

(10) Patent No.: US 8,076,084 B2
(45) Date of Patent: Dec. 13, 2011

(54) METHOD OF PREDICTING METASTATIC POTENTIAL PROGNOSIS OR OVERALL SURVIVAL OF CANCER PATIENTS

(75) Inventor: Kou-Juey Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 12/406,379

(22) Filed: Mar. 18, 2009

(65) Prior Publication Data

US 2010/0240031 A1    Sep. 23, 2010

(51) Int. Cl.
*C12Q 1/68*    (2006.01)
*G01N 33/53*    (2006.01)

(52) U.S. Cl. ........................ 435/6.14; 435/7.1

(58) Field of Classification Search .......... None
See application file for complete search history.

(56) References Cited

U.S. PATENT DOCUMENTS

2009/0092596 A1*    4/2009    Haley et al. ................ 424/130.1

OTHER PUBLICATIONS

Muh-Hwa Yang et al., "Direct Regulation of TWIST by HIF-1α Promotes Metastasis", Nature Cell Biology, vol. 10, No. 3, Mar. 2008, pp. 295-305.

* cited by examiner

*Primary Examiner* — James Martinell
(74) *Attorney, Agent, or Firm* — Hogan Lovells US LLP

(57) ABSTRACT

A method of predicting metastatic potential, prognosis or overall survival of cancer patients is provided. The method utilizes reliable markers, HIF-1α, TWIST or Snail, to predict the probability of the metastatic potential, prognosis situation or overall survival of cancer patients. Moreover, the method provided by the present invention can reach relatively higher predictability of metastatic potential, prognosis situation or overall survival as compared with the current markers.

3 Claims, 15 Drawing Sheets

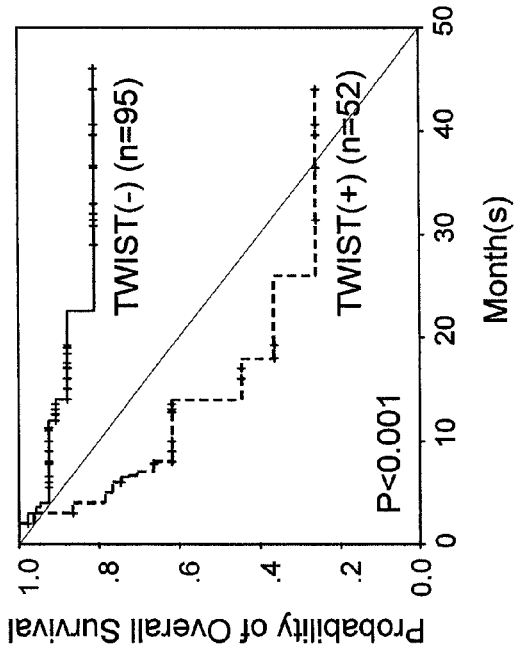
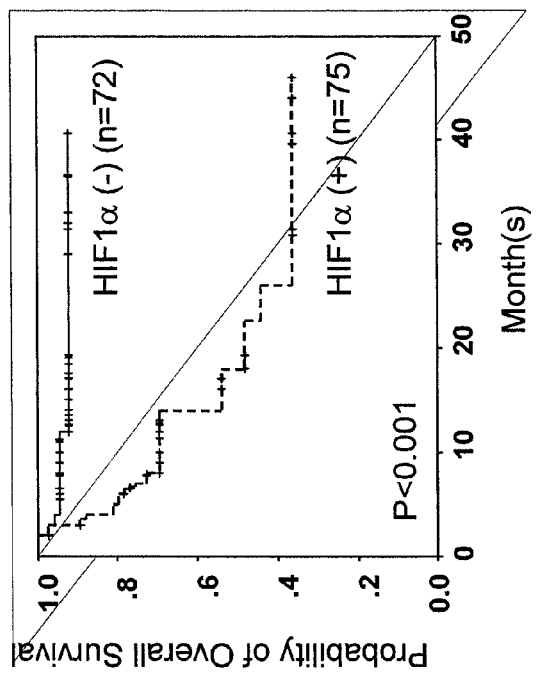
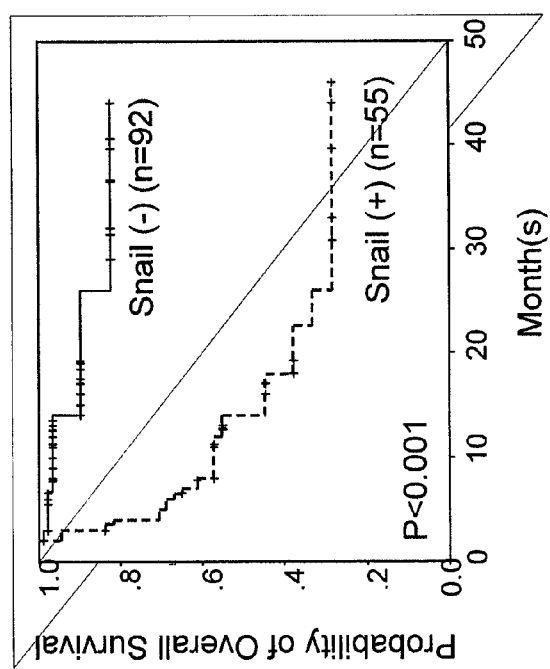
Fig. 4

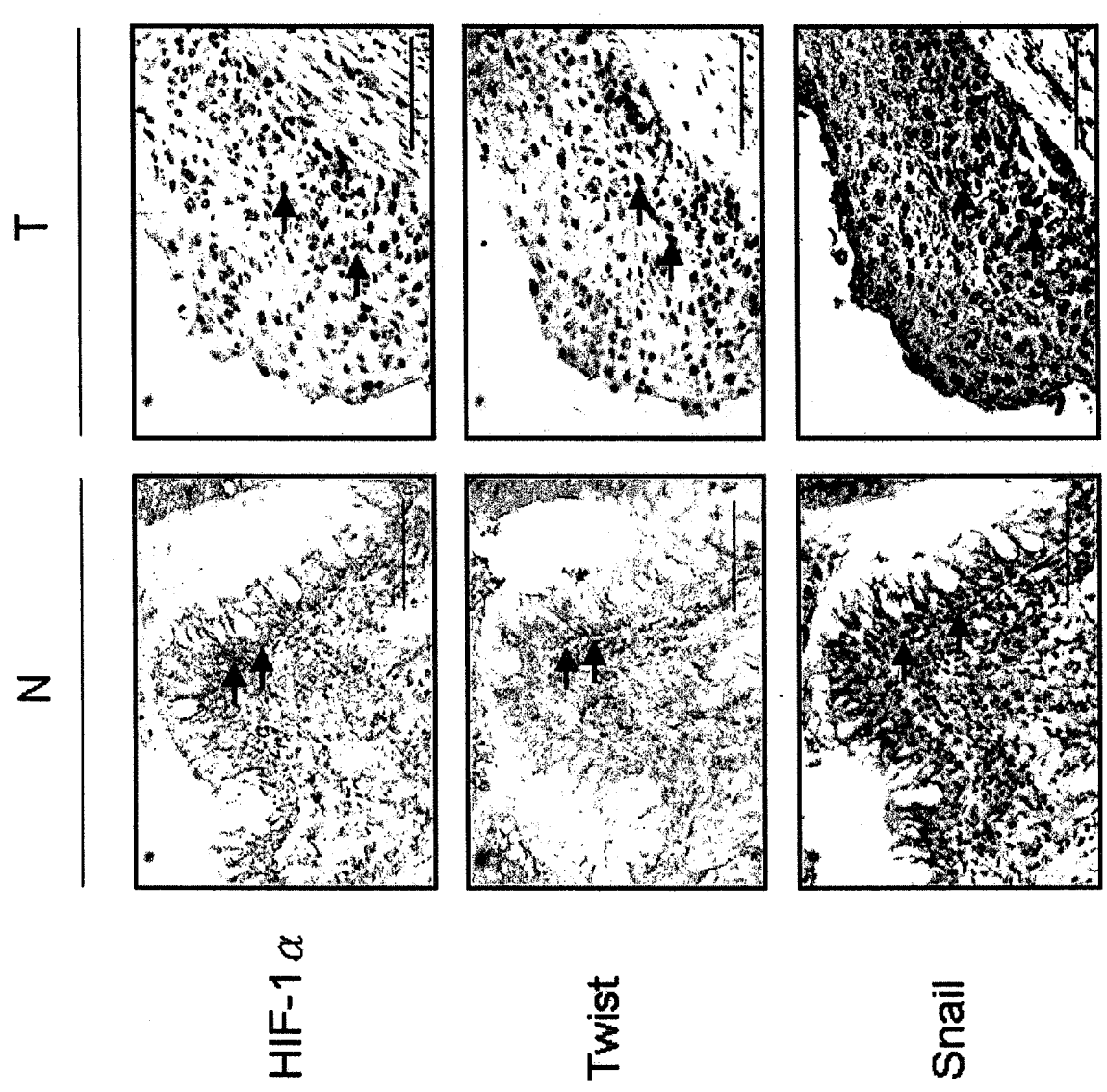

METHOD OF PREDICTING METASTATIC POTENTIAL PROGNOSIS OR OVERALL SURVIVAL OF CANCER PATIENTS

This application claims the benefit of priority under 35 U.S.C. §119 from the prior Japanese Patent Application JP 2009-056356, filed Mar. 10, 2009. The content of which is hereby incorporated by reference in its entirety.

FIELD OF THE INVENTION

The present invention relates to a method of predicting prognosis or overall survival of cancer patients, and more particularly, to a method of predicting prognosis or overall survival of cancer patients using a set of diagnostic markers.

BACKGROUND OF THE INVENTION

The current markers used to predict the prognosis or overall survival of cancer patients usually did not have high predictive value or were considered controversial due to conflicting reports (*Clin. Cancer Res.* 12, 507-515, 2006). That is to say, there are still no reliable markers or a set of diagnostic markers to significantly predict the prognosis or overall survival of cancer patients (*J. Exp. Pathol.* 86, 347-363, 2005; *Oral. Surg. Oral. Med. Oral. Pathol. Oral. Radio. Endod.* 102, 67-76, 2006).

Expression of hypoxic markers (HIF-1α, HIF-2α and CA IX) has been repeatedly reported to correlate with the development of therapeutic resistance and worse prognosis in different types of human cancers, including breast cancer, lung cancer, liver cancer, stomach cancer, kidney cancer, prostate cancer and so on (*Clin. Cancer Res.* 10, 8554-60, 2004; *J. Clin. Oncol.* 24, 727-35, 2006; *Inr. J. Cancer* 120, 1451-1458, 2007; *Morphol.* 14, 78-82, 2006; *Lung Cancer* 49, 325-335, 2005; *World J. Gastroenrerol II*, 1705-1708, 2005; *J. Heparol* 35, 643-649, 2005; *Clin. Cancer Res.* 12, 5112-5117, 2006; *Ann. Surg.* 243, 334-340, 2006; *Clin. Cancer Res.* 13, 7388-7393, 2007; *Clin. Cancer Res.* 11, 7658-7663, 2005; *Melanoma Res.* 13, 493-501, 2003). Specifically, tumors with abundant HIF-1 stabilization through intratumoral hypoxia are more likely to develop metastasis and correlate with poor survival (*J. Cell* 127, 679-695, 2006; *Cancer* 2, 38-47, 2002; *Trends Mol. Med.* 8 (4 Suppl), S62-67, 2002), especially in HNSCC (*Neck* 27, 622-638, 2005) and breast cancer (*Cancer Res.* 3, 313-317, 2001).

Increased expression levels of EMT regulators (TWIST, Snail, Slug, SIP1, E47, Zeb1) have also been reported to be associated with an aggressive phenotype and worse prognosis in different cancers, including breast cancer, liver cancer, stomach cancer and prostate cancer (*Cell* 117, 927-939, 2004; *Inr. J. Oncol.* 27, 1535-1541, 2005; *Anticancer Res.* 24, 3851-3856, 2004; *Oncogene* 21, 3241-3246, 2002; *Cancer* 103, 1631~1643, 2005; *Clin. Cancer Res.* 11, 8070-8078, 2005; *Clin. Cancer Res.* 12, 5369~5376, 2006; *Clin. Cancer Res.* 9, 2657-2664, 2003; *Pathology* 39, 470-475, 2007; *Am. J. Pathol.* 161, 1881-1891, 2002; *J. Pathol.* 211, 507-515, 2007; *Dig. Dis. Sci.* 50, 42-46, 2005; *Int. J. Cancer* 119, 2098-2104, 2006; *Histopathology* 50, 648-658, 2007; *Cancer Res.* 64, 5270-5282, 2004). Specifically, TWIST or Snail overexpression also correlates with a worse prognosis of cancer patients (*Cancer Cell* 8, 197-209, 2005; *Cell* 117, 927-939, 2004; *Clin. Cancer Res.* 12, 5369-5376, 2006; *Oncogene* 26, 1459-1467, 2007).

Despite the mentioned markers were shown as possible indicators for metastatic potential or worse prognosis of certain cancers, there are still no reports using a combination of markers such as hypoxic and EMT markers to analyze clinical samples and have a high probability of predicting prognosis and overall survival in cancer patients.

SUMMARY OF THE INVENTION

In consideration of the mentioned problem, it is an object of the present invention to provide a method of predicting metastatic potential of cancer patients.

It is another object of the present invention to provide at least two diagnostic markers selected from the group consisting of HIF-1α, TWIST and Snail, wherein the co-expression thereof can predict the metastatic potential of cancer patients with higher probability. The patients who co-expressed at least two diagnostic markers selected from the group consisting of HIF-1α, TWIST and Snail were predicted to have high probability of metastasis.

It is yet another object of the present invention to provide at least two diagnostic markers selected from the group consisting of HIF-1, TWIST and Snail, wherein the co-expression thereof can be served as an indicator for poor prognosis and lower overall survival of cancer patients.

Preferably, the head and neck squamous cell carcinoma (HNSCC) patients who co-express the three markers of HIF-1α, TWIST and Snail have more than 90% probability of metastasis.

Preferably, the HNSCC patients who co-expressed the three markers of HIF-1α, TWIST and Snail were considered having the worst prognosis and requiring the extensive therapeutic intervention.

Preferably, the non-small cell lung cancer (NSCLC) patients who co-express the two markers out of HIF-1α, TWIST and Snail have more than 50% probability of predicting poor overall survival.

According to the one object of the present invention, the present invention provides a method of predicting prognosis and overall survival potential of a cancer patient. The method comprises steps of obtaining a biological sample from the cancer patient; determining if at least two diagnostic markers selected from the group consisting of HIF-1α, TWIST and Snail are co-expressed in the biological sample; and comparing the diagnostic markers determined to be co-expressed in the biological sample with their absence in a control sample; wherein the co-expression of the diagnostic markers in the biological sample being indicators for the prognosis or the overall survival of the cancer patient. To explain further, a control sample is a group which does not co-express at least two diagnostic markers selected from the group consisting of HIF-1α, TWIST and Snail.

Preferably, the cancer is HNSCC.

Preferably, the cancer is NSCLC.

The co-expression of at least two diagnostic markers selected from the group consisting of HIF-1α, TWIST and Snail can provide relatively high predictability of metastasis for cancer patients as compared with current effective markers.

According to another object of the present invention, the present invention provides a method of predicting prognosis or overall survival of a cancer patient. The method comprises steps of obtaining a biological sample from the cancer patient; determining if at least two diagnostic markers selected from the group consisting of HIF-1α, TWIST and Snail are co-expressed in the biological sample; and comparing the diagnostic markers determined to be co-expressed in the biological sample with their absence in a control sample; wherein the co-expression of the diagnostic markers in the biological sample being indicators for the prognosis or the overall survival of the cancer patient.

Preferably, the cancer is HNSCC.

Preferably, the cancer is NSCLC.

The co-expression of at least two diagnostic markers selected from the group consisting of HIF-1α, TWIST and Snail can be served as indicators for poor prognosis or lower overall survival for cancer patients as compared with current effective markers.

These and other objects and features of the invention will become more fully apparent when the following detailed description is read in conjunction with the accompanying figures and examples.

BRIEF DESCRIPTION OF THE DRAWINGS

FIG. 4 depicts a diagram of probability of overall survival of HNSCC cases with HIF-1α(−) vs. HIF-1α(+), TWIST(−) vs. TWIST(+), and Snail(−) vs. Snail(+) in primary tumors of 147 HNSCC patients;

FIG. 7 depicts a diagram of a representative IHC staining of HIF-1α, TWIST and Snail markers among NSCLC patients;

DETAILED DESCRIPTION OF THE PREFERRED EMBODIMENTS

Embodiment 1

A Set of Diagnostic Markers for Head and Neck Squamous Cell Carcinoma (HNSCC)

In this embodiment, tissue-microarray immunohistochemistry analysis of HIF-1α, Snail and TWIST expressions was performed. (*Nature Cell Biology* 10, 295-305, 2008; *Oncogene* 26, 1459-1467, 2007).

1.1 Study Population, Sample collection and Tissue Microarray Construction

One hundred and forty-seven HNSCC patients who underwent treatment at Taipei Mackay Memorial Hospital and Taipei Veterans General Hospital between January 2001 and December 2004 were retrospectively analyzed. This study has been approved by the Institutional Review Board of Taipei Veterans General Hospital. The clinical characteristics of 147 HNSCC patients are illustrated in Table 1.

TABLE 1

Characteristics and univariate survival analysis of 147 HNSCC cases

| Variables | Case No. | Median OS (months) | P | Median RFS (months) | P |
|---|---|---|---|---|---|
| Age | | | 0.067 | | 0.211 |
| <50 | 60 | —* | | —* | |
| ≧50 | 87 | 26.0 | | 28.0 | |
| Gender | | | 0.354 | | 0.228 |
| male | 138 | —* | | —* | |
| female | 9 | —* | | —* | |
| T stage | | | 0.004 | | <0.001 |
| 1~2 | 68 | —* | | —* | |
| 3~4 | 79 | 26 | | 18 | |
| N stage | | | <0.001 | | <0.001 |
| 0 | 100 | —* | | —* | |
| 1-3 | 47 | 18 | | 18 | |
| HIF-1α overexpression | | | <0.001 | | <0.001 |
| Yes | 75 | 18 | | 14 | |
| No | 72 | —* | | —* | |
| TWIST overexpression | | | <0.001 | | <0.001 |
| Yes | 52 | 14 | | 8 | |
| No | 95 | —* | | —* | |
| Snail overexpression | | | <0.001 | | <0.001 |
| Yes | 55 | 14 | | 8 | |
| No | 92 | —* | | —* | |

Abbreviations:
OS, overall survival;
RFS, relapse-free survival;
*Median survival was not reached.

Primary tumor samples and the corresponding non-cancerous matched tissue were obtained during surgery; whereas 56 metastatic tumor samples (34 of visceral metastasis and 22 of cervical nodes) were obtained when metastasis occurred. A high-density tissue microarray (TMA) was constructed as described (*Oncogene* 26, 1459-1467, 2007).

1.2 Immunohistochemstry (IHC)

The sample processing and IHC procedure were performed as described (*Oncogene* 26, 1459-1467, 2007). The interpretation of HIF-1α, CA IX, Snail and TWIST IHC results was performed independently by two pathologists according to the criteria described previously (*Oncogene* 26, 1459-1467, 2007; *J. Clin. Oncol* 24, 727-735, 2006; *Clin. Cancer Res.* 8, 2595-2604, 2002; *Int. J. Cancer* 120, 1451-1458, 2007; *J. Urol.* 177, 1258-1263, 2007; *Genes Dev.* 13, 2207-2217, 1999).

Figure 1:
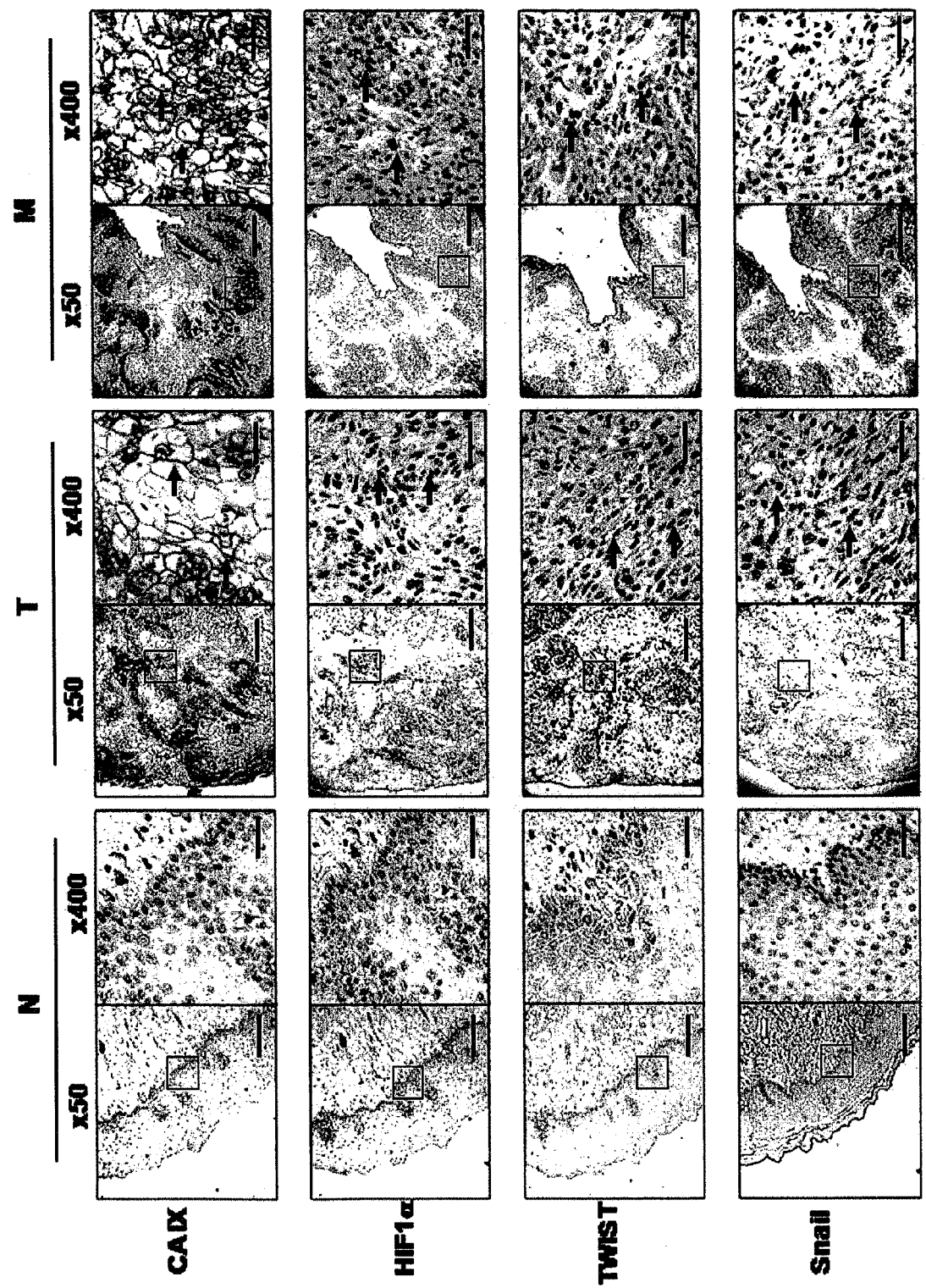
FIG. 1 depicts a diagram of IHC analysis of co-expression of CA IX, HIF-1α, TWIST and Snail in corresponding normal tissue (N), primary tumor (T) and metastatic tumor (M) of a representative HNSCC case (the black arrows indicate the nuclear expression of HIF-1α, TWIST and Snail; whereas the red arrows indicate the membranous expression of CA IX)

A representative case of IHC staining of all four markers was shown in FIG. 1. The functional indicator of HIF-1α, carbonic anhydrase IX (CA IX) (*J. Clin. Oncol* 24, 727-735, 2006; *Clin. Cancer Res.* 8, 2595-2604, 2002; *Int. J. Cancer* 120, 1451-1458, 2007), was stained in all samples to further correlate the hypoxic zones of tumors. The result showed that tumors with ≧50% hypoxic areas (CA IX≧50% staining) significantly correlated with HIF-1α overexpression (≧50% HIF-1α nuclear expression in tumor cells) (P=0.001, data not shown). It was confirmed that there is good correlation between HIF-1α and CA IX IHC results, which is consistent with previous reports (*Clin. Cancer Res.* 8, 2595-2604, 2002; *Int. J. Cancer* 120, 1451-1458, 2007).

Figure 2:
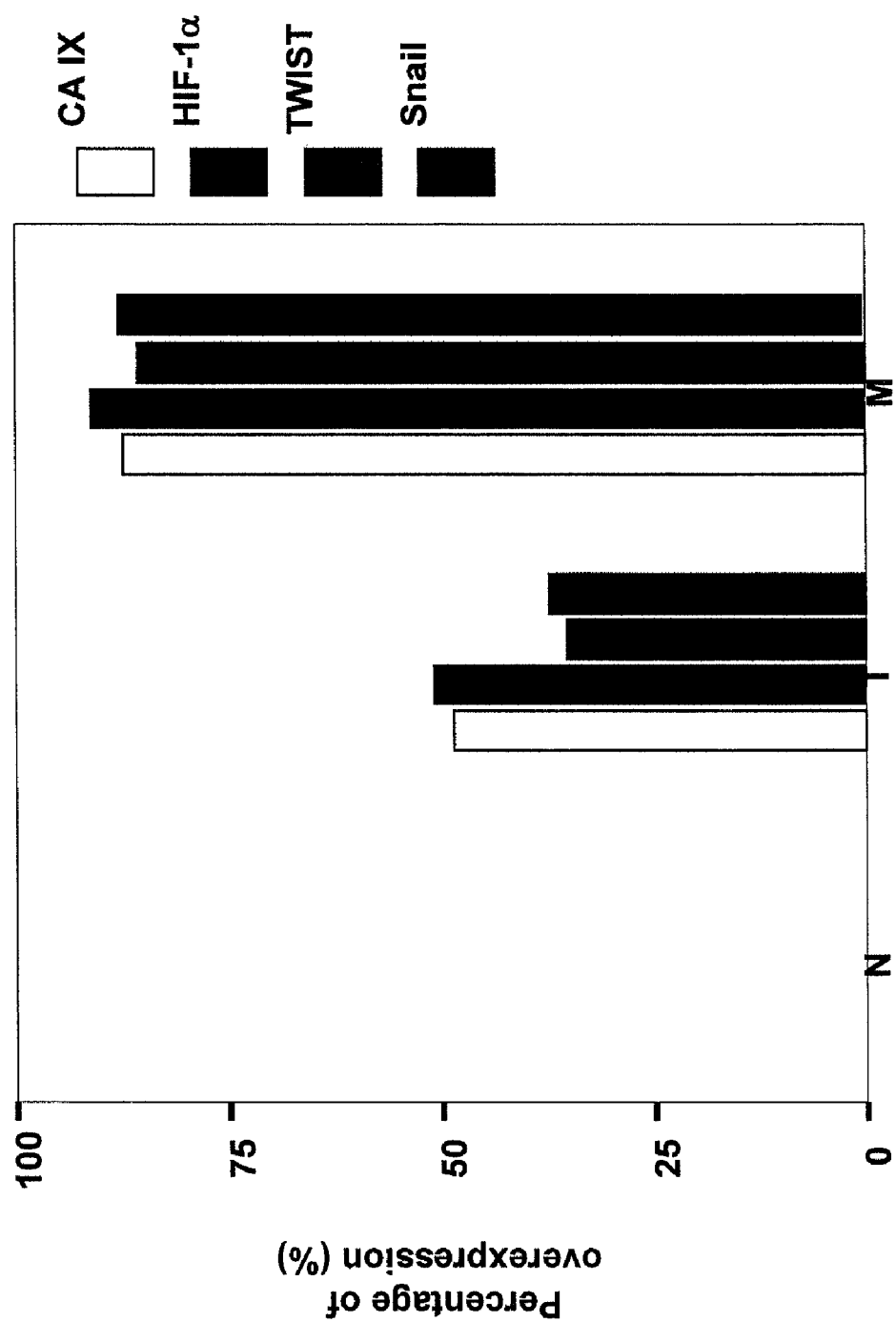
FIG. 2 depicts a diagram of the percentage of IHC positivity of CA IX, HIF-1α, TWIST and Snail in the N (normal tissue), T (tumor tissue) and M (metastatic tumor) samples of HNSCC cases.

FIG. 2 depicts the percentage of IHC positivity of CA IX, HIF-1α, TWIST and Snail in the N (normal tissue), T (tumor tissue), and M (metastatic tumor) samples of HNSCC cases. This result also identified the patient group with hypoxic tumors (48.3% of primary and 91.1% of metastatic HNSCCS). TWIST and Snail overexpression (≧50% nuclear expression in tumor cells) was shown in 35.4% and 37.4% of primary tumors and in 85.7% and 82.1% of metastatic ones, respectively. Considering the correlation between tumor hypoxia or HIF-1α overexpression and activation of TWIST or Snail, tumors with more than 50% hypoxic areas significantly correlated with TWIST or Snail overexpression (a representative case shown in FIG. 1; P<0.001, 0.001, respectively) (data not shown).

The mentioned results indicated that tumor hypoxia correlated with HIF-1α overexpression and consequentially with TWIST and Snail expression. In addition, a higher proportion of HIF-1α, TWIST, or Snail expression was observed in metastatic tumor samples than in primary ones (FIG. 2).

1.3 The Intensity of HIF-1α Expression Correlates with the Respective Expression of TWIST and Snail The immunoreactivity of HIF-1α, TWIST and Snail was graded from 0 to 3+ (0, no staining; 1+, 1~25%; 2+, 26~50%; 3+, >50% nuclear staining) according to nuclear expression, and only 3+ (>50% nuclear staining) was considered as a positive IHC result (*Oncogene* 26, 1459-1467, 2007; *J. Clin. Oncol* 24, 727-735, 2006; *Clin. Cancer Res.* 8, 2595-2604, 2002; *Int. J. Cancer* 120, 1451-1458, 2007; *J. Urol.* 177, 1258-1263, 2007; *Genes Dev.* 13, 2207-2217, 1999).

The correlation of the IHC expression gradient of HIF-1α, TWIST and Snail in primary tumor samples of 147 HNSCC cases is illustrated in Table 2, which indicated that the expression gradient of HIF-1α also correlated significantly with that of TWIST or Snail (P<0.001, <0.001, respectively).

TABLE 2

Correlation of the IHC expression gradient of HIF-1α, TWIST, and Snail in primary tumor samples of 147 HNSCC cases

| | | HIF-1α IHC gradient | | | | |
|---|---|---|---|---|---|---|
| | | 0 | 1 | 2 | 3 | P |
| TWIST IHC gradient | 0 | 33 | 10 | 0 | 9 | <0.001 |
| | 1 | 1 | 9 | 2 | 6 | |
| | 2 | 0 | 3 | 12 | 10 | |
| | 3 | 0 | 0 | 2 | 50 | |

TABLE 2-continued

Correlation of the IHC expression gradient of HIF-1α, TWIST, and Snail in primary tumor samples of 147 HNSCC cases

| | | HIF-1α IHC gradient | | | | |
|---|---|---|---|---|---|---|
| | | 0 | 1 | 2 | 3 | P |
| Snail IHC gradient | 0 | 32 | 8 | 3 | 0 | <0.001 |
| | 1 | 0 | 12 | 1 | 18 | |
| | 2 | 0 | 0 | 5 | 13 | |
| | 3 | 2 | 2 | 7 | 44 | |

1.4 Statistical Analysis

The independent Student's t-test was used to compare the continuous variables between two groups, and the $\chi^2$ test was applied for comparison of dichotomous variables. The Kaplan-Meier estimate was used for metastasis-free and overall survival analysis, and the log-rank test was used to compare the difference. The Cox's proportional hazards model was applied in multivariate survival analysis to test independent prognostic factors. The control groups of all the statistical analyses were usually the first groups in the panels unless specified otherwise in the figure legends. The level of statistical significance was set at 0.05 for all tests.

Figure 3:
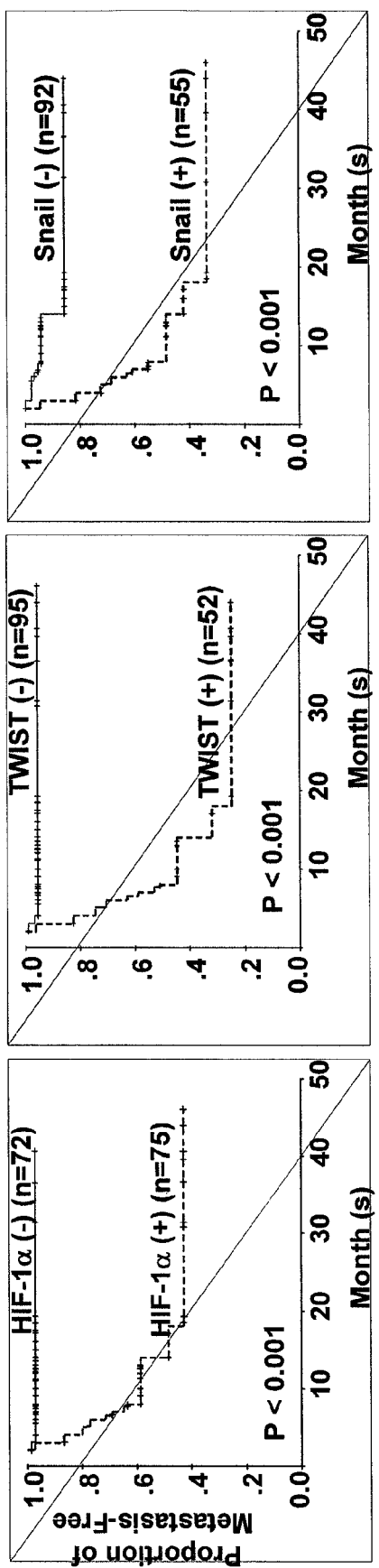
FIG. 3 depicts a diagram of Kaplan-Meier analysis of metastasis-free period of HNSCC cases with HIF-1α(−) vs. HIF-1α(+), TWIST(−) vs. TWIST(+), and Snail(−) vs. Snail (+) in primary tumors of 147 HNSCC patients.

There was no statistical difference in the expression pattern of HIF-1α, TWIST, and Snail between the metastatic samples obtained from cervical nodes or visceral organ (data not shown). For metastasis and survival analysis, overexpression of HIF-1α, TWIST or Snail in primary HNSCCs was associated with a shorter metastasis-free period (FIG. 3), and the same situation was observed in the overall survival analysis (P<0.001, <0.001, <0.001, respectively) (FIG. 4). It is shown that the respective overexpression of HIF-1α, TWIST and Snail in HNSCC patients could result in lower probability of overall survival.

Figure 5:
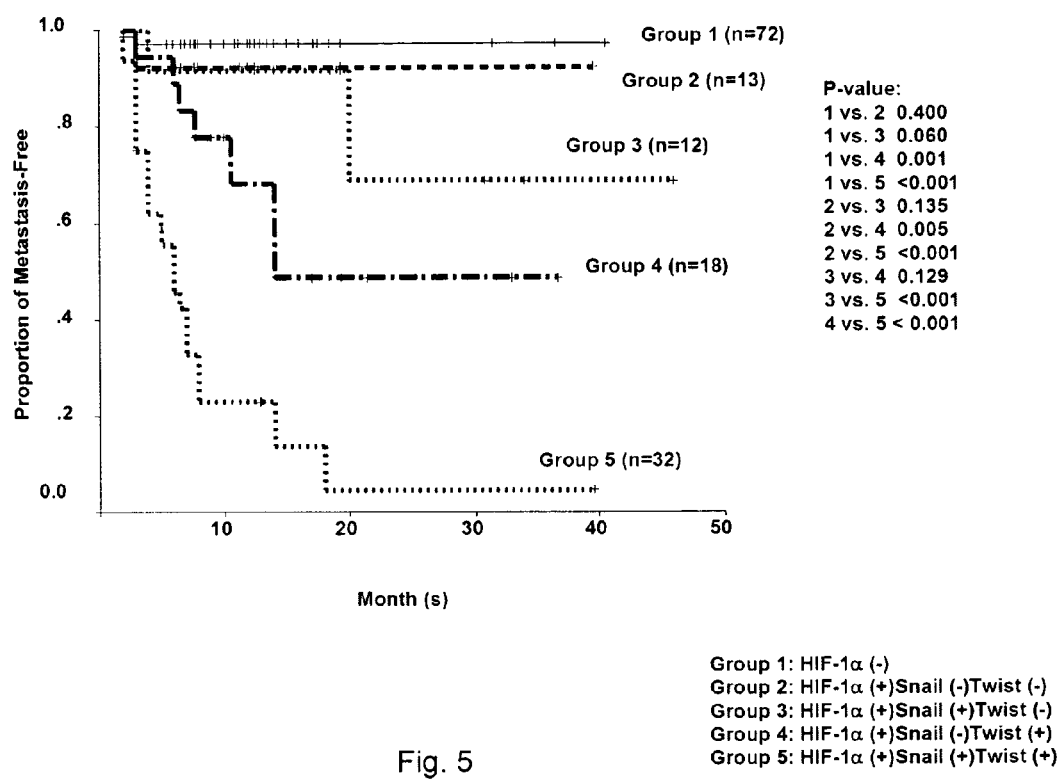
FIG. 5 depicts a diagram of Kaplan-Meier analysis of metastasis-free period of HNSCC cases with HIF-1α(−), HIF-1α(+) vs. Snail(−) vs. Twist(−), HIF-1α(+) vs. Snail(+) vs. Twist(−), HIF-1α(+) vs. Snail(−) vs. Twist (+), HIF-1α(+) vs. Snail(+) vs. Twist(+) in primary tumors of 147 HNSCC patients.
Figure 6:
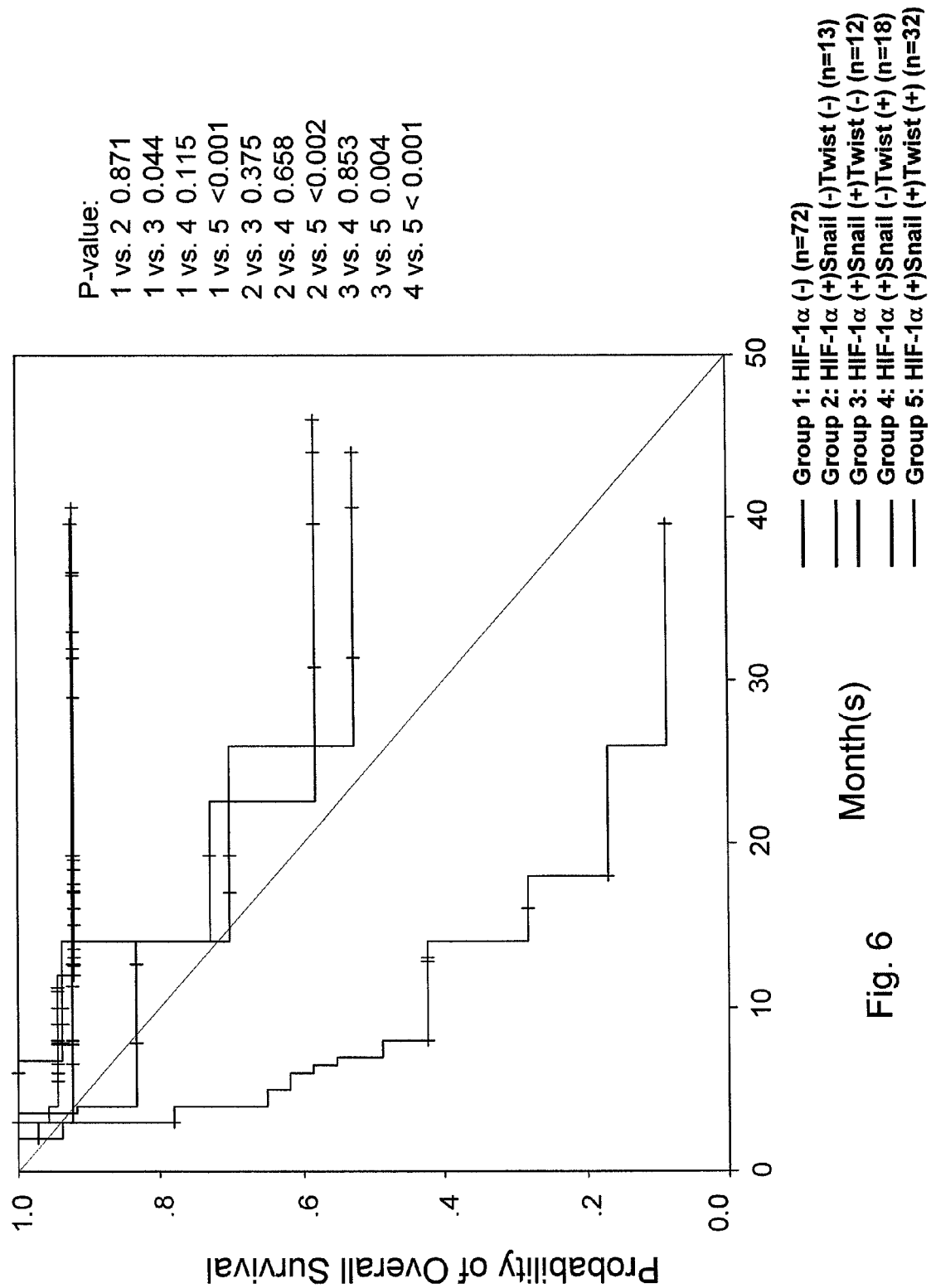
FIG. 6 depicts a diagram of probability of overall survival of HNSCC cases with with HIF-1α(−), HIF-1α(+) vs. Snail (−) vs. Twist(−), HIF-1α(+) vs. Snail(+) vs. Twist(−), HIF-1α (+) vs. Snail(−) vs. Twist (+), HIF-1α(+) vs. Snail(+) vs. Twist(+) in primary tumors of 147 HNSCC patients.

Furthermore, to investigate the prognostic significance of the expression pattern of HIF-1α, TWIST, and Snail in HNSCCs, HNSCC patients were divided into five groups based on the expression profile of HIF-1α, TWIST and Snail: (1) HIF-1α(−); (2) HIF-1α(+)Snail(−)TWIST(−); (3) HIF-1α(+)Snail(+)TWIST(−); (4) HIF-1α(+)Snail(−)TWIST(+); and (5) HIF-1α(+)Snail(+)TWIST(+). Kaplan-Meier metastasis-free curves were generated and the log-rank test was used to test for significant difference among groups. The results showed that the groups 3 and 4 have the shorter metastasis-free period and co-expression of HIF-1α, TWIST, and Snail (Group 5) exhibited the shortest metastasis-free period as compared therewith (FIG. 5). That is, more than 90% patients of Group 5 had been diagnosed with metastasis. Similar pattern was observed in the overall survival analysis, which also showed that more than 90% patients of Group 5 died (FIG. 6). The mentioned results demonstrated that activation of TWIST and/or Snail by HIF-1α to promote metastasis indeed occurred in HNSCC patients and co-expression of HIF-1α, TWIST and Snail was associated with the most aggressive outcome.

In this embodiment, it was evident that the activation of TWIST and/or Snail by HIF-1α indeed occurs in HNSCC cancers and the expression profile of HIF-1α, TWIST and Snail could be used as an evaluative indicator for the prognostic significance of cancer patients. That is, co-expression of HIF-1α, TWIST, and Snail could be used as a valuable marker to predict prognosis or overall survival in HNSCC patients.

Embodiment 2

A Predictive Marker Set for Non-Small Cell Lung Cancer (NSCLC)

HIF-1α overexpression was noted in 62% of primary NSCLC tumors, and was marginally associated with poor prognosis (*Br J Cancer,* 85:881-90, 2001). HIF-1α mRNA expression was shown to be prognostic in early-stage NSCLC (*J Clin Oncol.,* 25:5562-9, 2007). In the embodiment, to investigate the relationship between HIF-1α, TWIST and Snail in lung cancer cells, tissue-microarray immunohistochemistry analysis of HIF-1α, TWIST and Snail expressions was performed.

2.1 Study Population, Sample Collection and Tissue Microarray Construction

Eighty-seven NSCLC patients who underwent surgical resection at Taipei Mackay Memorial Hospital and Taipei Veterans General Hospital between January 2003 and December 2004 were retrospectively analyzed. This study has been approved by the Institutional Review Board of Taipei Veterans General Hospital. The clinical characteristics of 87 NSCLC patients are illustrated in Table 3.

2.2 Immunohistochemstry (IHC)

The same procedures were performed as in Embodiment 1. The immunoreactivity of HIF-1α, Twist and Snail was graded from 0 to 3+ (0, no staining; 1+, 1~25% nuclear staining; 2+, 26~50% nuclear staining; 3+, >50% nuclear staining) and only 3+ (>50% nuclear staining) was considered as a positive IHC result. A representative case of IHC staining of all markers in NSCLC was shown in FIG. 7.

According to Table 1, the overexpression profiles of HIF-1α, Twist and Snail in 87 NSCLC specimens by IHC were 28/87 (32.2%), 32/87 (36.8%) and 48/87 (55.2%), respectively.

2.3 Statistical Analysis

Figure 8A:
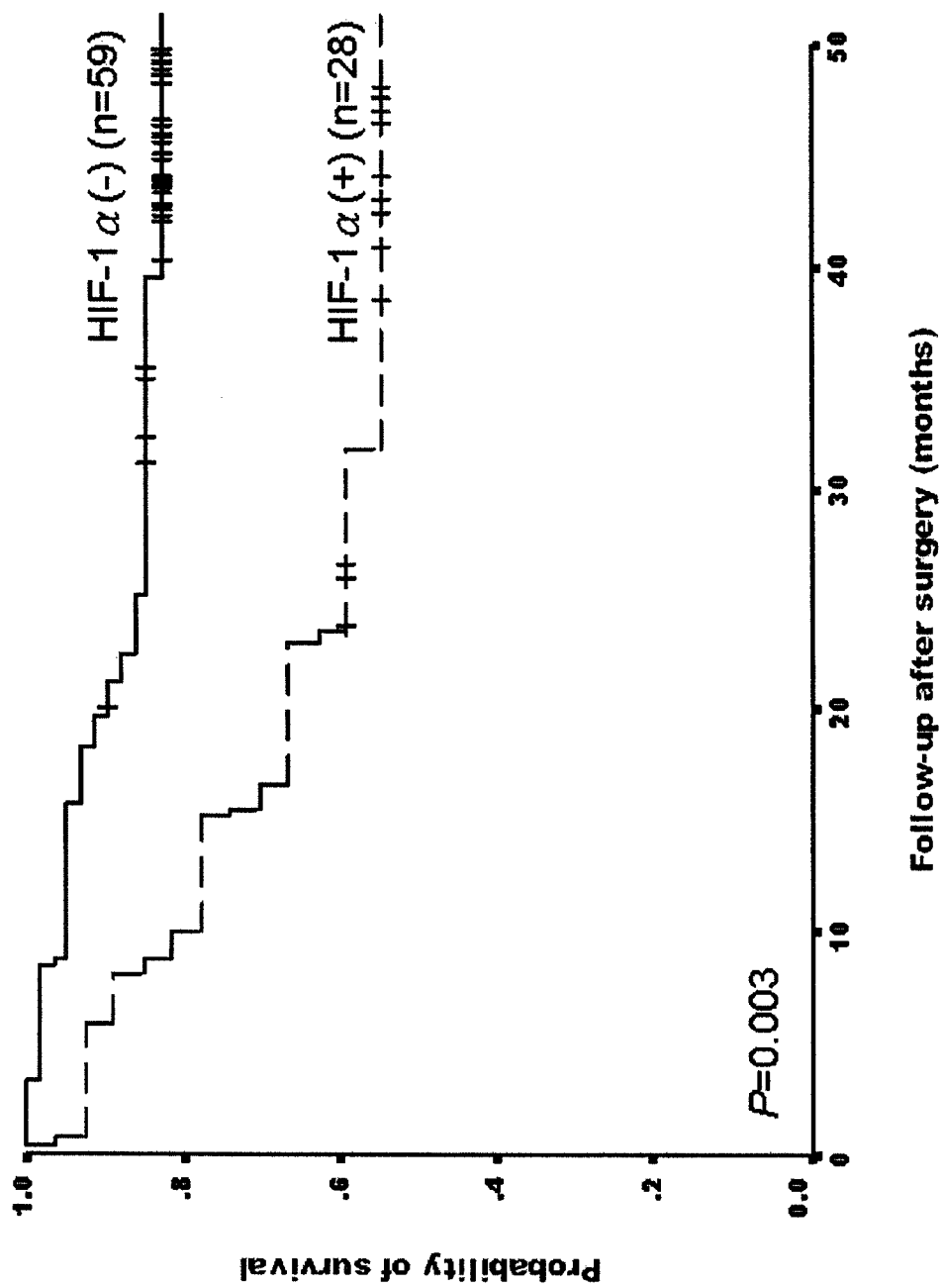
FIG. 8 depicts a diagram of Kaplan-Meier analysis of survival rate of NSCLC cases with (a) HIF-1α(−) vs. HIF-1α (+), (b) TWIST(−) vs. TWIST(+), and (c) Snail(−) vs. Snail (+) in primary tumors of 87 NSCLC patients.
Figure 8B:
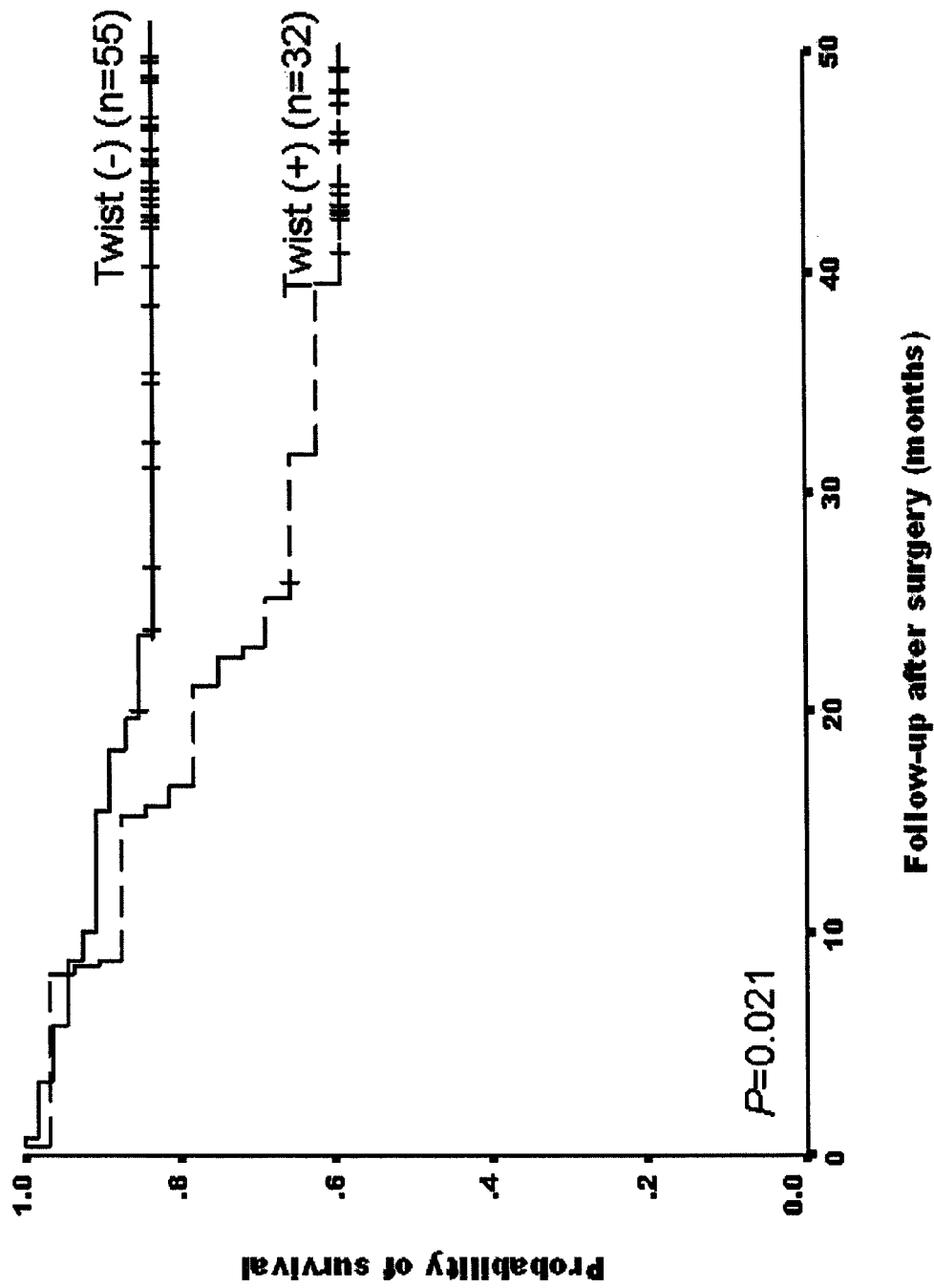
Figure 8C:
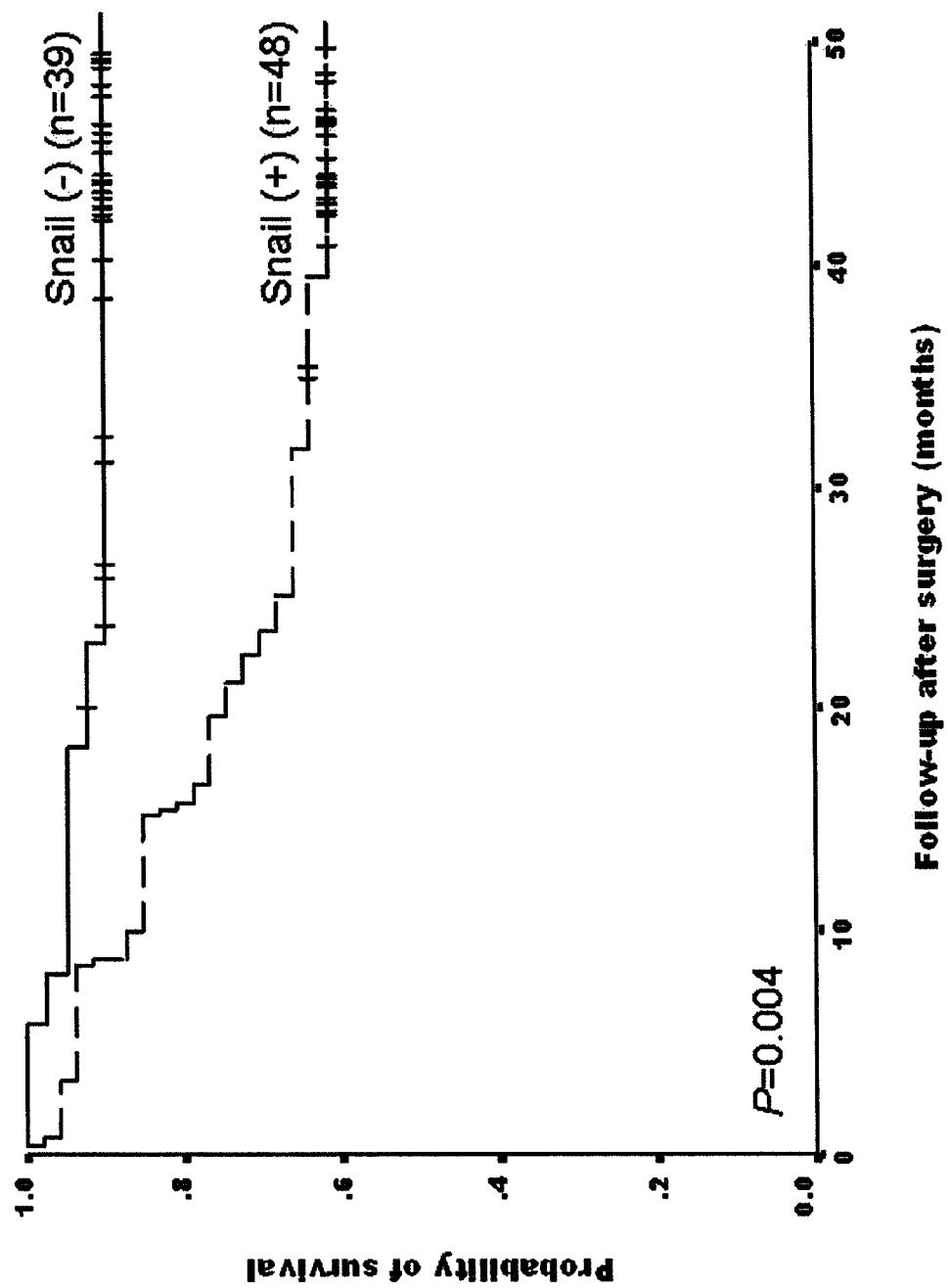
Figure 9A:
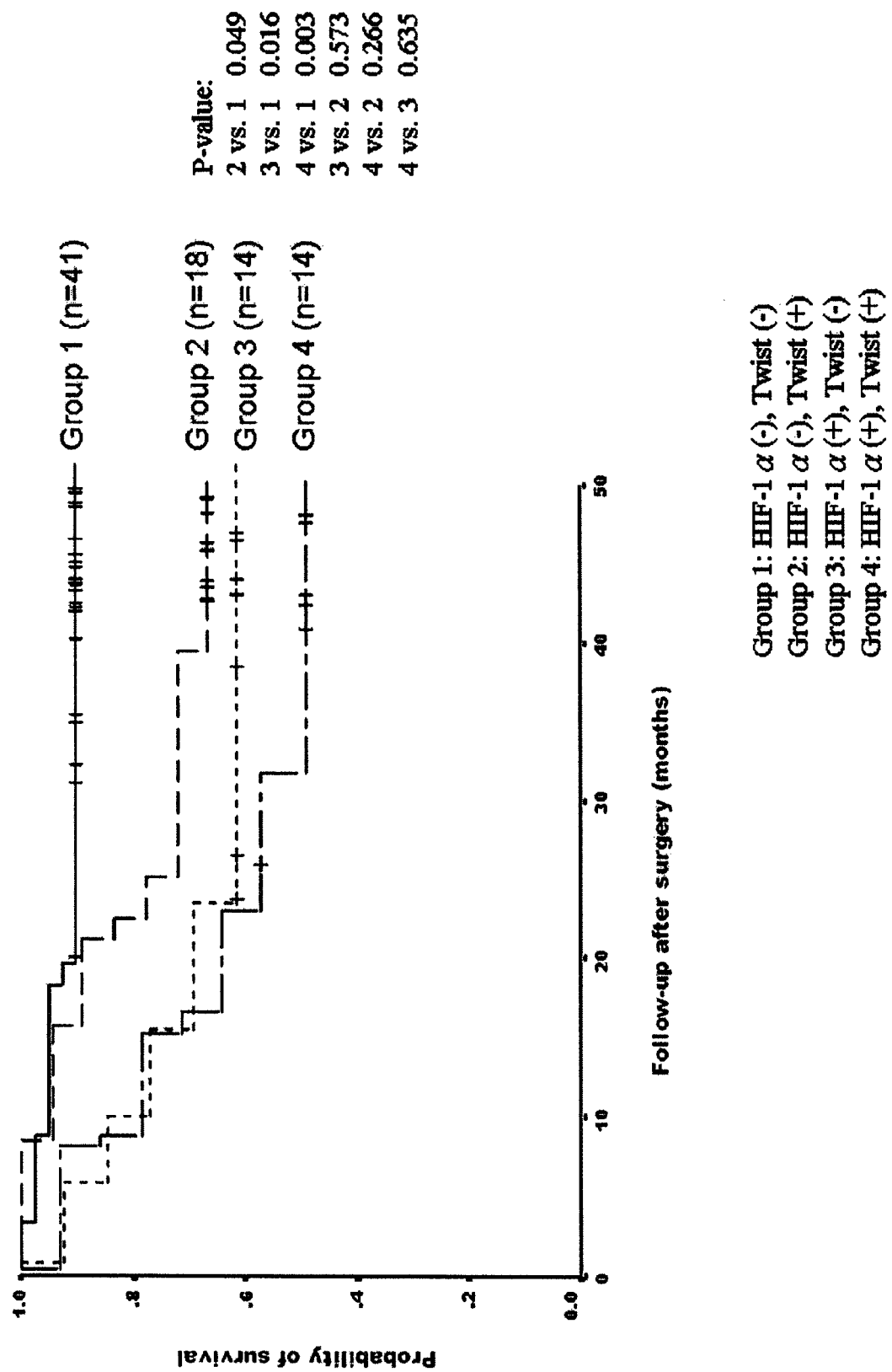
FIG. 9 depicts a diagram of the subgroup analysis of 87 NSCLC cases according to the expression profile of HIF-1α, TWIST, and Snail, wherein (a) shows the expression profile of HIF-1α and TWIST; (b) shows that of HIF-1α and Snail; and (c) shows that of TWIST and Snail.
Figure 9B:
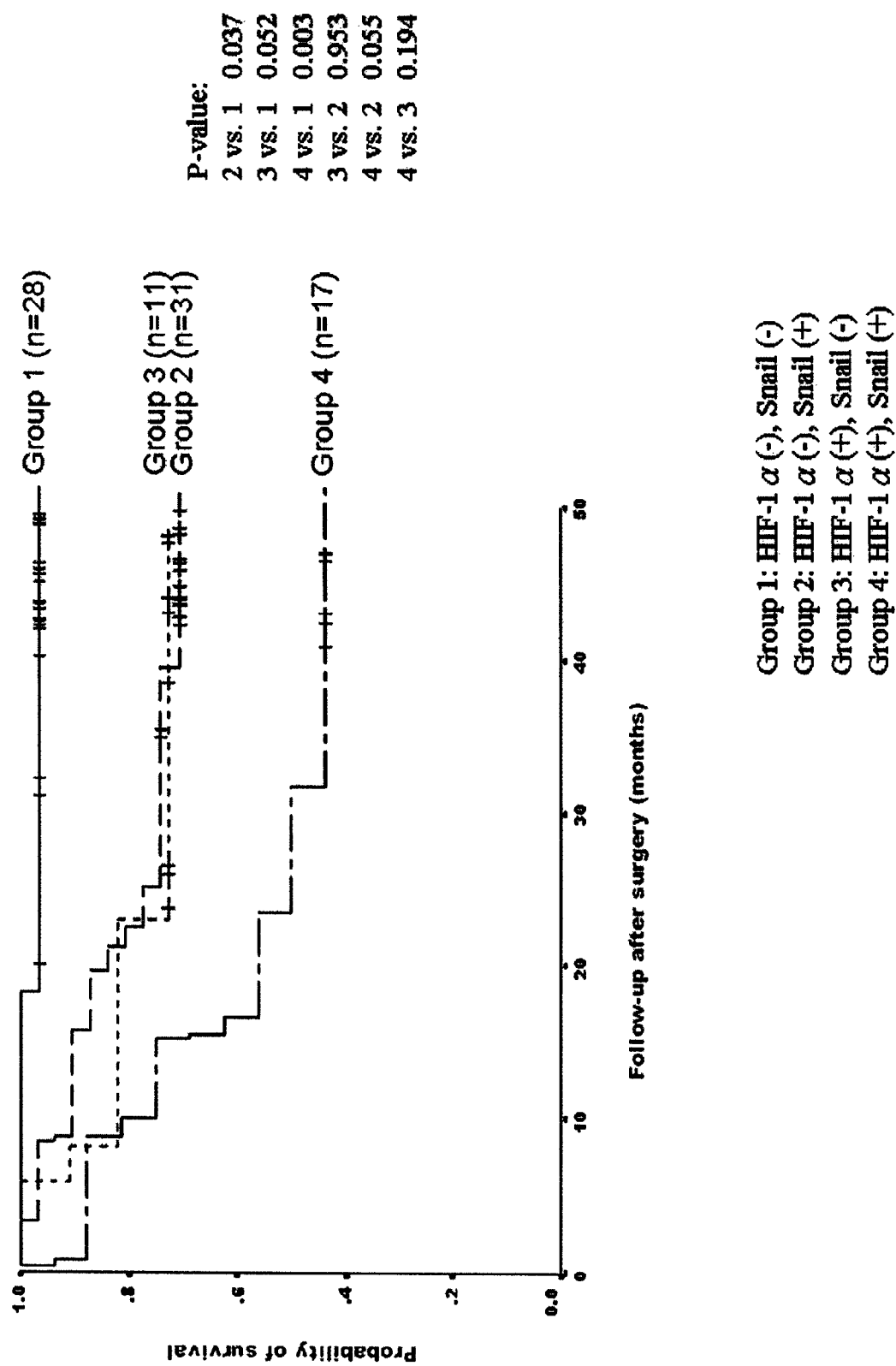
Figure 9C:
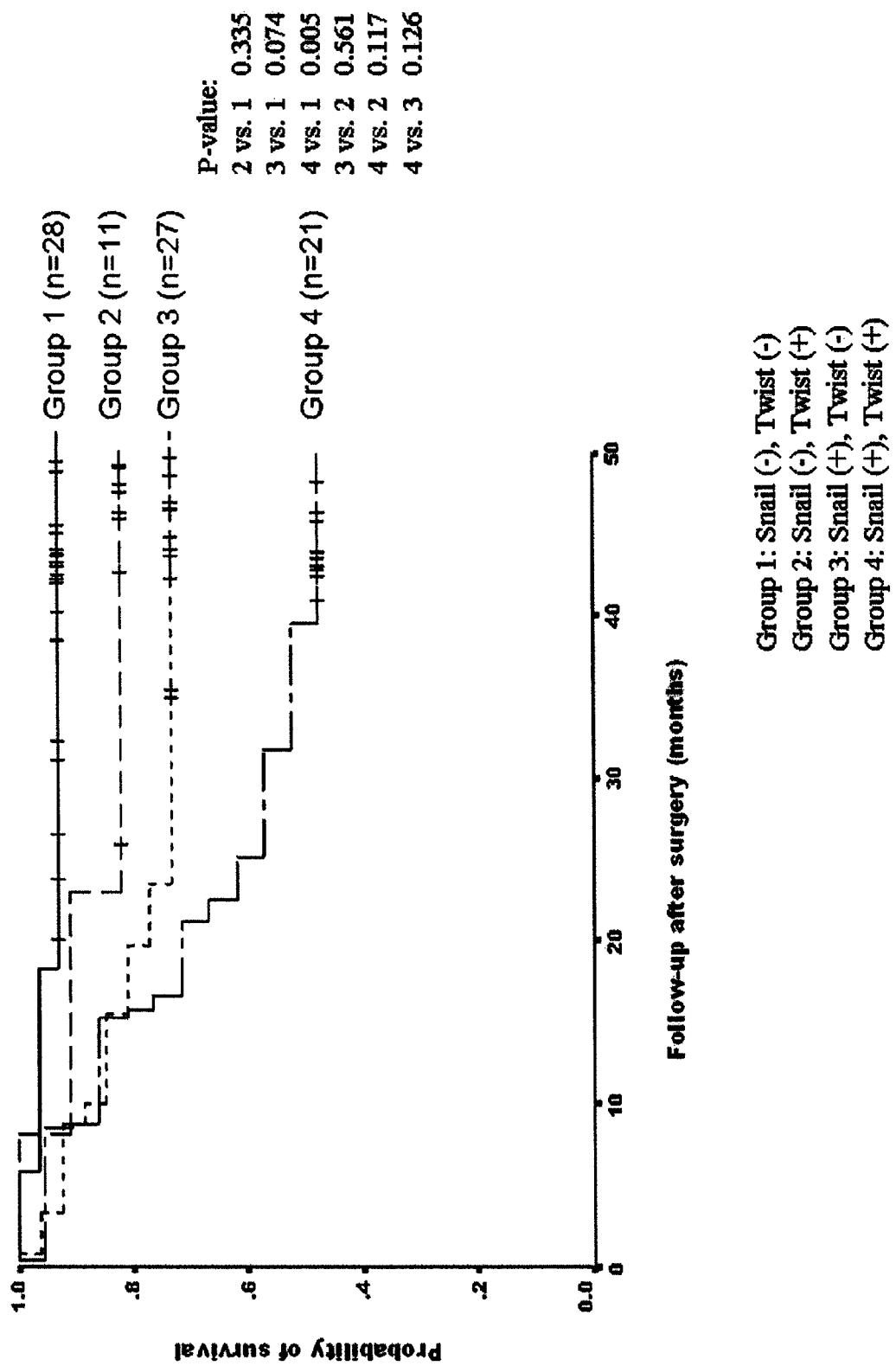
Figure 10A:
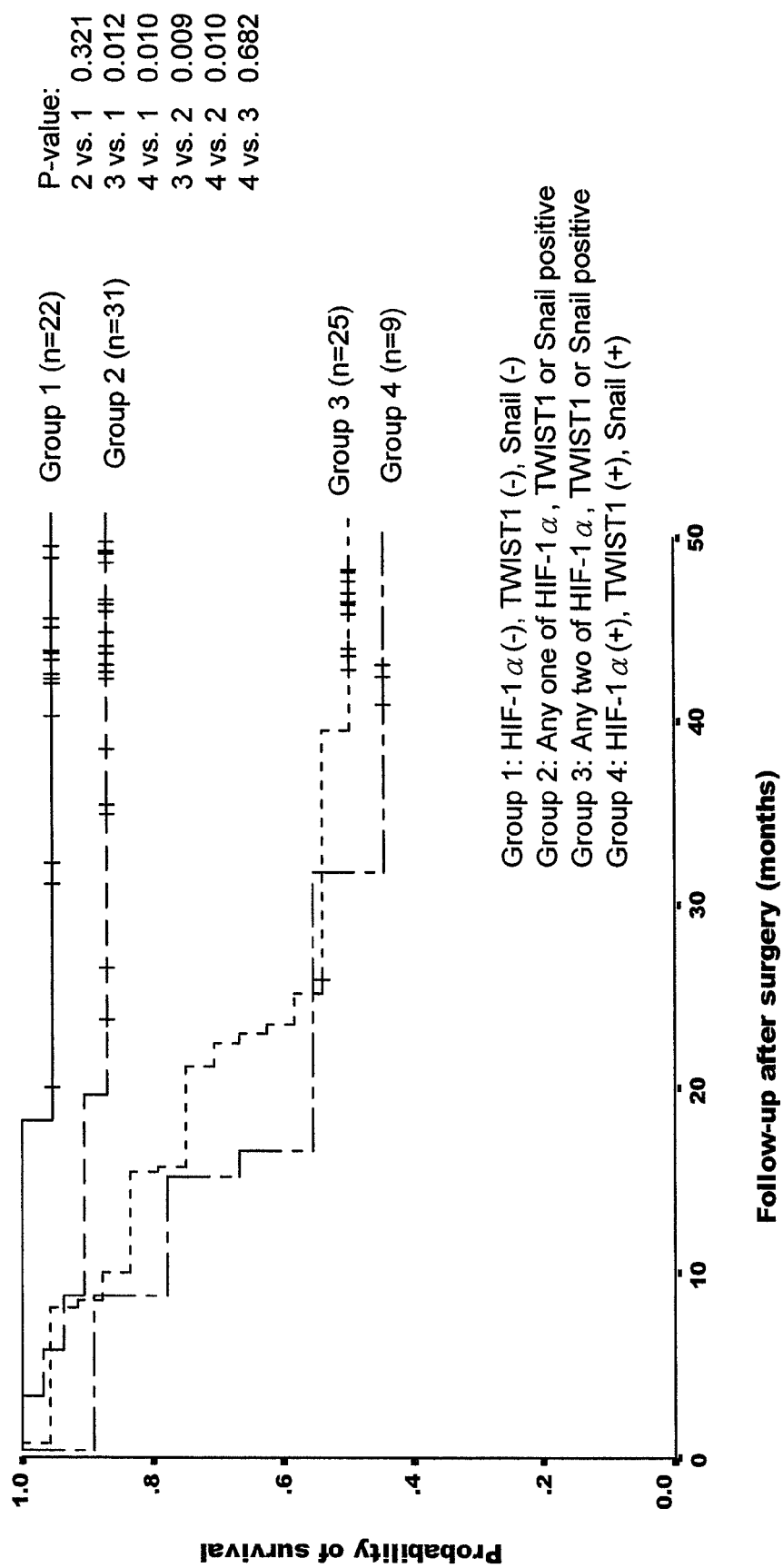
FIG. 10 depicts a diagram of Kaplan-Meier survival analysis in NSCLC patients according to the number of markers including HIF-1α, TWIST and Snail which had increased expression, wherein (a) the patients were divided into four groups: HIF-1α(−)/TWIST1(−)/Snail(−) (group1), any one of HIF-1α, TWIST1 or Snail overexpression (group 2), any two of HIF-1α, TWIST1 or Snail overexpression (group 3), and HIF-1α(+)/TWIST1(+)/Snail(+) (group 4); and (b) the patients were re-divided into two groups: None or one of HIF-1α, TWIST or Snail overexpression (group 1), and any two or all of HIF-1α, TWIST or Snail overexpression (group 2).
Figure 10B:
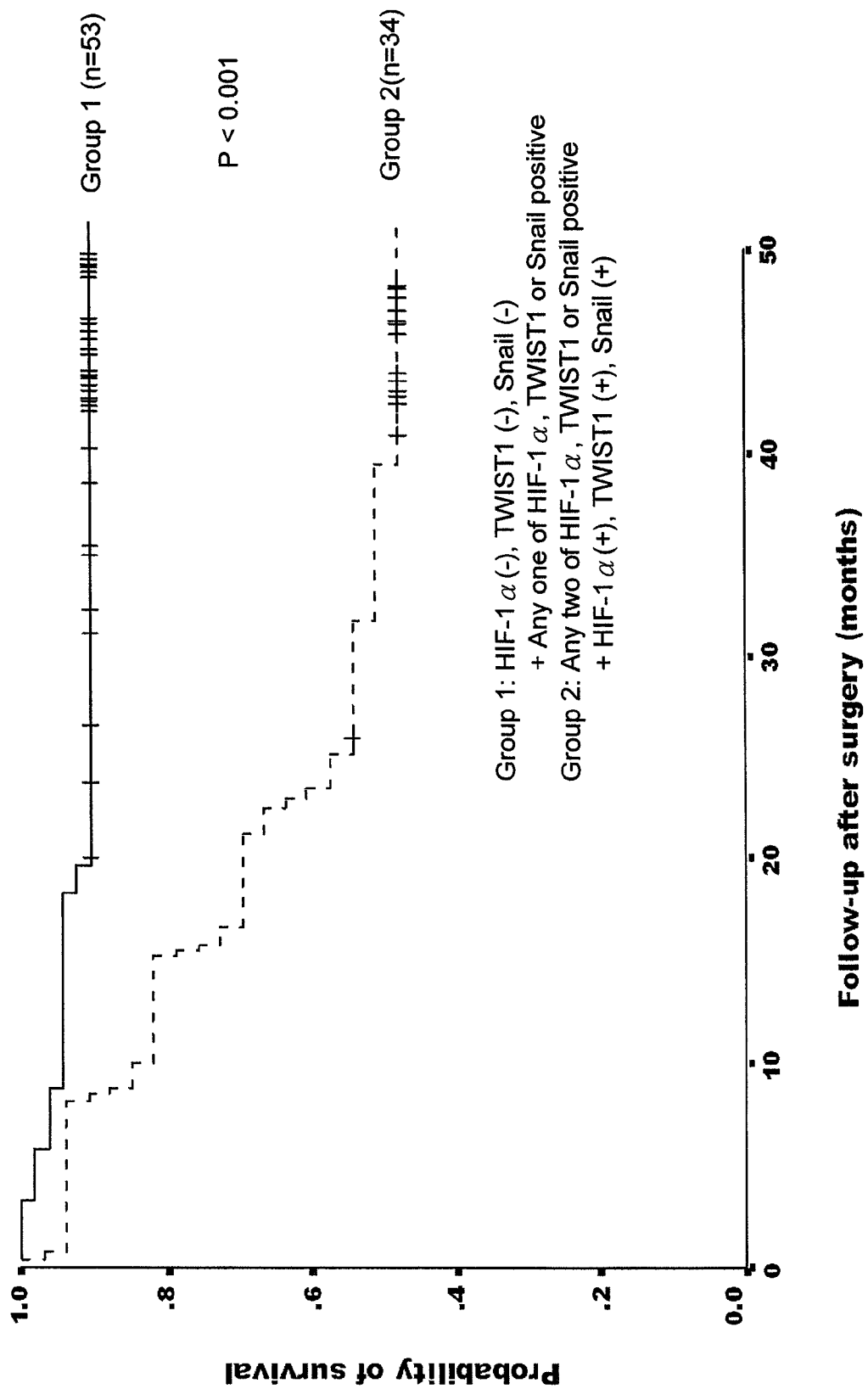

The same statistical methods to the embodiment 1 were used herein. For survival analysis shown in FIGS. 8(*a*)-(*c*), the respective overexpression of HIF-1α, TWIST and Snail in NSCLCs were associated with a shorter overall survival. Furthermore, to investigate the prognostic significance of the co-expression pattern of any two of HIF-1α, TWIST, and Snail markers in NSCLCs, subgroup analysis of NSCLC cases was shown in FIGS. 9(*a*)-(*c*). From FIG. 10(*a*), any two of HIF-1α, TWIST or Snail overexpression (Group 3) and HIF-1α(+)/TWIST1(+)/Snail(+) (group 4) had a shorter overall survival when compared with the other groups. Further, from FIG. 10(*b*), co-expression of any two or all of HIF-1α, TWIST and Snail (Group 2) had a significantly worse overall survival. Therefore, based on the result of FIG. 10, co-expression of two or three markers out of HIF-1α, TWIST and Snail had a worse prognosis and overall survival than no-expression or expression of one marker.

TABLE 3

Characteristics and univariate survival analysis of 87 NSCLC patients

| Variables | Case No. | Median OS (months) | P | HIF-1α, TWIST, Snail expression | | P |
|---|---|---|---|---|---|---|
| | | | | None or one (%) (n = 53) | Two or three (%) (n = 34) | |
| Age | | | 0.856 | | | 0.550 |
| <65 | 25 | —* | | 14 (56.0) | 11 (44.0) | |
| ≧65 | 62 | 53.5 | | 39 (62.9) | 23 (37.1) | |
| Gender | | | 0.371 | | | 0.600 |
| male | 69 | 53.5 | | 43 (62.3) | 26 (37.7) | |
| female | 18 | —* | | 10 (55.6) | 8 (44.4) | |
| T stage | | | 0.004 | | | 0.752 |
| 1~2 | 73 | —* | | 45 (61.6) | 28 (38.4) | |
| 3~4 | 14 | 23 | | 8 (57.1) | 6 (42.9) | |
| N stage | | | 0.012 | | | 0.947 |
| 0 | 49 | —* | | 30 (61.2) | 19 (38.3) | |
| 1-3 | 38 | 53.5 | | 23 (60.5) | 15 (39.5) | |
| Histological type | | | 0.213 | | | 0.063 |
| Adenocarcinoma | 54 | 53.5 | | 37 (68.5) | 17 (31.5) | |
| Non-adenocarcinoma | 33 | | | 16 (48.5) | 17 (51.5) | |
| Extent of pulmonary reseciton | | | 0.09 | | | 0.154 |
| Lobectomy or widget resection | 79 | | | 50 (63.3) | 29 (36.7) | |
| Pneumonectomy or bilobectomy | 8 | 16.6 | | 3 (37.5) | 5 (62.5) | |
| HIF-1α overexpression | | | 0.03 | | | |
| Yes | 28 | —* | | | | |
| No | 59 | —* | | | | |
| TWIST overexpression | | | 0.021 | | | |
| Yes | 32 | —* | | | | |
| No | 55 | —* | | | | |
| Snail overexpression | | | 0.004 | | | |
| Yes | 48 | 53.3 | | | | |
| No | 39 | —* | | | | |

*Median survival was not reached.

In this embodiment, it was also evident that the activation of TWIST and/or Snail by HIF-1α indeed occurs in NSCLC cancers and co-expression of at least two markers out of HIF-1α, TWIST and Snail could be used as evaluative indicators for the prognostic significance thereof.

In the present invention the IHC technique was used to analyze the situation of cancer patients, but the same result can be obtained by other kinds of analytical techniques, such as RT-PCR or Real-time PCR, and the scope of the present invention, therefore, should not be limited thereto.

Based on the above, the present invention provides at least two diagnostic markers selected from the group consisting of HIF-1α, TWIST and Snail as a set of reliable markets to predict the the prognosis or the overall survival of cancer patients.

It can be known from the aforementioned preferred embodiment of the present invention, as is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure.

What is claimed is:

1. A method of predicting prognosis or overall survival of a non-small cell lung cancer (NSCLC) patient, comprising:
    obtaining a biological sample from the cancer patient;
    performing a detection sequence to detect HIF-1α marker;
    performing a detection sequence to detect TWIST marker or Snail marker;
    if HIF-1α and TWIST are co-expressed in the biological sample at a level higher than in a control sample known to lack expression of these markers, determining that the patient is an elevated risk for having non-small cell lung cancer; and
    if HIF-1α and Snail are co-expressed in the biological sample at a level higher than in a control sample known to lack expression of these markers, determining that the patient is an elevated risk for having non-small cell lung cancer
    wherein co-expression of said HIF-1α and TWIST or said HIF-1α and Snail markers in the biological sample indicates poor prognosis or overall survival of the cancer patient.

2. A method of predicting prognosis or overall survival of a nonsmall cell lung cancer (NSCLC) patient, comprising:
    performing a detection sequence to detect HIF-1α marker in a biological sample of said NSCLC patient;
    performing a detection sequence to detect TWIST or Snail marker in said biological sample;
    analyzing said biological sample of said NSCLC patient to determine the expression level of HIF-1α marker in the sample;
    analyzing said biological sample of said NSCLC patient to determine the expression level of TWIST marker or Snail marker in the sample;
    comparing the expression level of said HIF-1α marker to the expression level of said HIF-1α marker in a control sample,
    comparing the expression level of said TWIST or Snail marker to the expression level of the TWIST or Snail marker in said control sample;
    wherein if the expression levels of said at least two diagnostic markers HIF-1α marker and said TWIST marker in the biologic sample are all higher than their counterparts in the control sample, a poor prognosis or overall survival is predicted; and
    wherein if the expression levels of said HIF-1α marker and said Snail marker in the biologic sample are higher than their counterparts in the control sample, a poor prognosis or overall survival is predicted.

3. The method of claim 2, further comprising analyzing all three diagnostic markers, and comparing expression levels of all three diagnostic markers.

* * * * *